(12) United States Patent
Caban

(10) Patent No.: US 9,743,869 B2
(45) Date of Patent: Aug. 29, 2017

(54) OPTICAL ISOLATION ELEMENT FOR IMPLANTABLE SENSOR

(71) Applicant: Senseonics, Incorporated, Germantown, MD (US)

(72) Inventor: Allan Caban, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 197 days.

(21) Appl. No.: 14/676,957

(22) Filed: Apr. 2, 2015

(65) Prior Publication Data

US 2015/0282740 A1 Oct. 8, 2015

Related U.S. Application Data

(60) Provisional application No. 61/973,912, filed on Apr. 2, 2014.

(51) Int. Cl.
| | |
|---|---|
| *A61B 5/1455* | (2006.01) |
| *A61B 5/1459* | (2006.01) |
| *A61B 5/00* | (2006.01) |
| *A61B 5/07* | (2006.01) |

(52) U.S. Cl.
CPC .......... *A61B 5/1459* (2013.01); *A61B 5/0084* (2013.01); *A61B 5/686* (2013.01); *A61B 5/6861* (2013.01); *A61B 5/0031* (2013.01); *A61B 5/0071* (2013.01); *A61B 5/076* (2013.01); *A61B 2562/0233* (2013.01); *A61B 2562/0238* (2013.01); *A61B 2562/162* (2013.01); *A61B 2562/185* (2013.01)

(58) Field of Classification Search
CPC .............. A61B 5/1455; A61B 5/14556; A61B 5/14532; A61B 5/68; A61B 5/6846; A61B 5/6847; A61B 5/686; A61B 5/6861
See application file for complete search history.

(56) References Cited

U.S. PATENT DOCUMENTS

| | | | |
|---|---|---|---|
| 6,748,254 B2 * | 6/2004 | O'Neil ............... | A61B 5/14551 600/310 |
| 8,290,557 B2 * | 10/2012 | Davis ................. | A61B 5/14532 600/310 |
| 8,515,507 B2 * | 8/2013 | Rabinovitz .......... | A61B 5/0084 600/310 |
| 2013/0211213 A1 | 8/2013 | DeHennis et al. | |

* cited by examiner

*Primary Examiner* — Eric Winakur
(74) *Attorney, Agent, or Firm* — Rothwell, Figg, Ernst & Manbeck, P.C.

(57) ABSTRACT

An optical isolation element is provided on an optical sensor comprising a light source, at least one photodetector, and indicator material that emits light that is detected by the photodetector when optically excited by the light source. The optical isolation element limits the optical paths by which light may be transmitted by the light source, thereby limiting exposure of the excitation light source to regions of interest. The optical isolation element also limits the optical paths by which light may be transmitted to the photodetector, thereby limiting exposure of the photodetector to light from extraneous sources.

9 Claims, 7 Drawing Sheets

OPTICAL ISOLATION ELEMENT FOR IMPLANTABLE SENSOR

PRIORITY CLAIM

This application claims the benefit under 35 U.S.C. §119(e) of the filing date of provisional patent application Ser. No. 61/973,912 filed Apr. 2, 2014, the disclosure of which is incorporated herein by reference in its entirety.

FIELD OF THE DISCLOSURE

This disclosure relates to sensors and, more particularly, sensors having photodetectors for detecting light emissions from a reference material and an optical isolation element for preventing or limiting the amount of extraneous light, not emitted by the reference material, from impinging upon the photodetectors.

BACKGROUND

Implantable sensors, such as optical, chemical or biochemical sensors, are known which can be implanted within a living animal and which measure the presence or concentration of an analyte or substance of interest in a medium within the living animal. Optical sensors may include one or more light sources, such as one or more LEDs, one or more photodetectors, such as one or more photodiodes, and a layer of indicator molecules that emit a detectable optical signal, e.g., fluoresce, when optically excited by the light source. The light source(s) emits an excitation light signal that impinges upon the indicator molecules, and the indicator molecules emit a signal (which can be a function of the presence and/or concentration of the analyte of interest if present), at least some of which impinges upon the photodetector(s), which convert the detected light into an electrical signal.

An exemplary sensor of this type is described in United States Patent Application Publication No. 2013/0211213, the disclosure of which is hereby incorporated by reference.

Current sensor configurations allow for light other than that emitted by the indicator molecules, such as ambient light, to impinge on the photodetector(s) from a variety of angles. This "stray" light impinging upon the photodetector(s) adds noise to the measurements. Current sensor configurations also tend to lose much of the desired excitation light to areas of the sensor which are not statistically relevant to light measurement calculation.

To subtract out the undesired stray light signals and reduce signal noise due to such stray light, current sensor configurations employ light filters and/or algorithm calculations to subtract out stray light noise and/or employ the location of the indicator molecules relative to the optics components to maximize incident excitation light and detected emission light while minimizing stray light signals.

It thus would be desirable to more effectively block the incidence of stray light signals onto the photodetectors of a sensor and to more effectively control the dispersal of the excitation light.

SUMMARY

Aspects of the disclosure embody an optical isolation element that can be attached to the electronics assembly inside a sensor. The element can be configured and oriented in a manner that at least partially surrounds the optics elements so as to concentrate the excitation light to a specific area of the indicator molecule matrix relative to the location and orientation of the photodetectors that is most relevant to emission signal detection. This can be achieved by, in some embodiments, affixing the optical isolation element to a portion of the senor or by providing a close slip fit between the optical isolation element and the optics elements. The element is preferably opaque so that it will block stray external light from outside sources that normally could be detected by the photodetectors and add noise to the measurements generated by the sensor. Undesired light paths can be blocked or filled in with opaque materials such as overfills, underfills, epoxies, or paints. The optical isolation element can be machined or molded, and it can be made of any suitable material that is sufficiently opaque, is moldable or machinable, and is non-reactive with other components or materials within the sensor. In certain embodiments, suitable materials include plastic, metal, acrylic, glass, porcelains, epoxies, nylon, or Delrin.

According to aspects of the disclosure, a sensor for detecting the presence and/or concentration of a substance of interest comprises at least one excitation light source, indicator material positioned and oriented with respect to the excitation light source to receive excitation light emitted therefrom and configured to emit an optical signal when excited by the excitation light source and when contacted by the substance of interest, one or more optical detector elements positioned and oriented with respect to the indicator material to receive at least a portion of the optical signal emitted by the indicator material, and an optical isolation element partially surrounding the light source and the optical detector elements and formed of a material configured to substantially prevent the passage of light therethrough. The optical isolation element is positioned and oriented with respect to the light source, the optical detector elements, and the indicator material and includes an opening formed therein so as to permit at least a portion of the light emitted by the excitation light source to impinge upon the indicator material and to permit at least a portion of the light emitted by the indicator material to impinge upon the optical detector element.

According to further aspects, the sensor comprises a housing enclosing the light source, the optical detector elements, and the optical isolation element, and the indicator material is disposed on or embedded in at least a portion of the housing.

According to further aspects, the optical isolation element is formed from an opaque material.

According to further aspects, the optical isolation material is formed from a material selected from the group consisting of: plastic, metal, acrylic, glass, porcelains, epoxies, Delrin, or nylon.

According to further aspects, the optical isolation element comprises first and second opposed end walls and first and second opposed side walls.

According to further aspects, the optical isolation element is at least partially shaped to conform to an inner surface of the housing.

According to further aspects, the housing has a cylindrical shape, and the optical isolation element comprises first and second end walls that are generally parallel to each other and oriented so as to be perpendicular to a longitudinal axis of the housing and first and second side walls, each extending between the first and second end walls and each being curved so as to conform to a curvature of the housing.

According to further aspects, the sensor further comprises a planar substrate on which the light source and the optical detector elements are mounted, and the optical isolation element is cooperatively attached to the substrate so as to substantially prevent light from passing between the optical isolation element and the substrate.

According to further aspects, gaps between the optical isolation element and other components of the sensor are filled with opaque materials such as overfills, underfills, epoxies, or paints.

Other features and characteristics of the disclosed optical isolation element, as well as the methods of operation, functions of related elements of structure and the combination of parts will become more apparent upon consideration of the following description and the appended claims with reference to the accompanying drawings, all of which form a part of this specification, wherein like reference numerals designate corresponding parts in the various figures.

BRIEF DESCRIPTION OF THE DRAWINGS

The accompanying drawings, which are incorporated herein and form part of the specification, illustrate various, non-limiting embodiments of the optical isolation element. In the drawings, common reference numbers indicate identical or functionally similar elements.

DETAILED DESCRIPTION OF PREFERRED EMBODIMENTS

Figure 1:
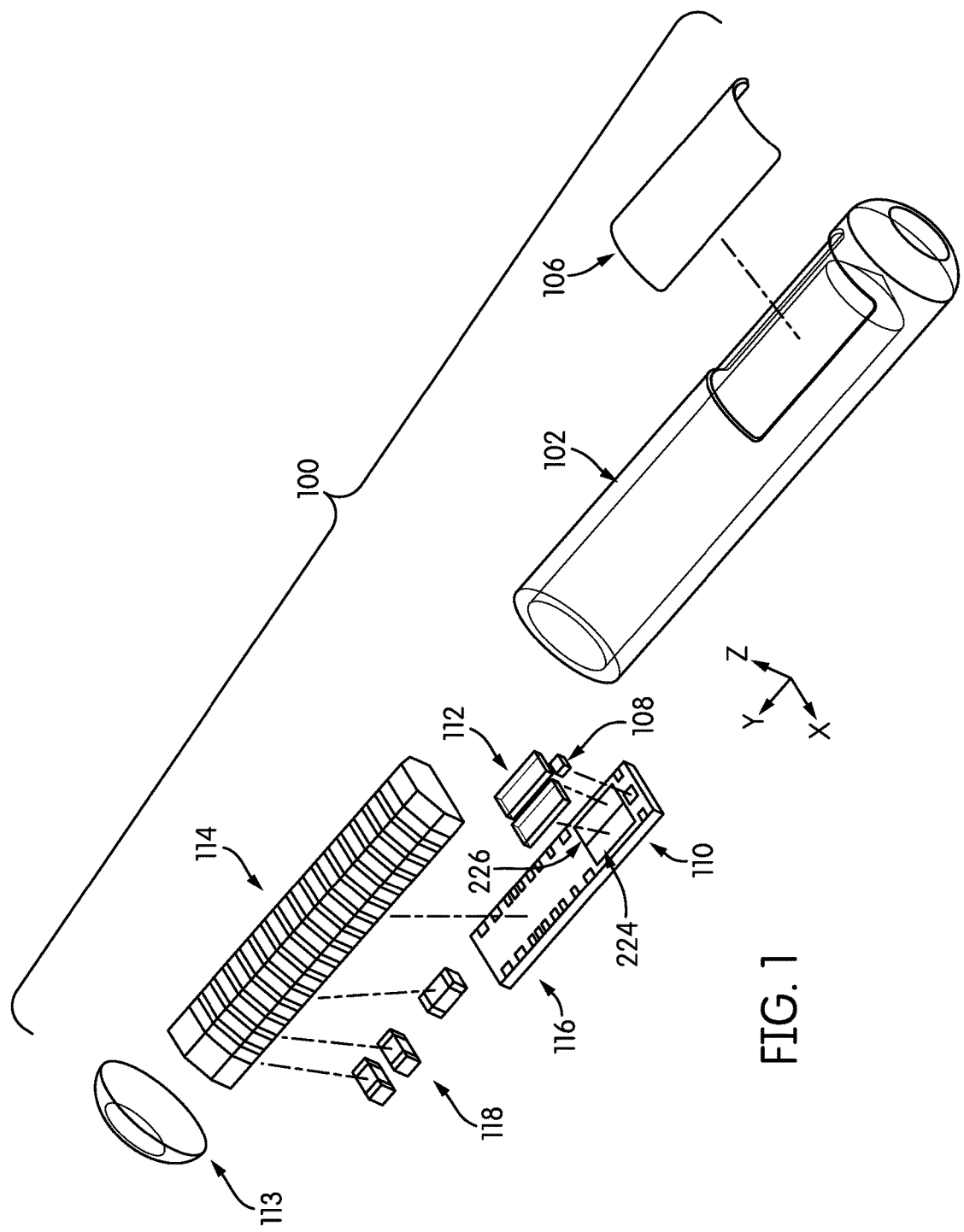
FIG. 1 is an exploded perspective view of a sensor of the type in which an optical isolation element embodying aspects of the optical isolation element may be employed.

This description may use relative spatial and/or orientation terms in describing the position and/or orientation of a component, apparatus, location, feature, or a portion thereof. Unless specifically stated, or otherwise dictated by the context of the description, such terms, including, without limitation, top, bottom, above, below, under, on top of, upper, lower, left of, right of, in front of, behind, next to, adjacent, between, horizontal, vertical, diagonal, longitudinal, transverse, etc., are used for convenience in referring to such component, apparatus, location, feature, or a portion thereof in the drawings and are not intended to be limiting.

Furthermore, unless otherwise stated, any specific dimensions mentioned in this description are merely representative of an exemplary implementation of an optical isolation element and are not intended to be limiting. Unless otherwise indicated or the context suggests otherwise, as used herein, "a" or "an" means "at least one" or "one or more."

Figure 2:
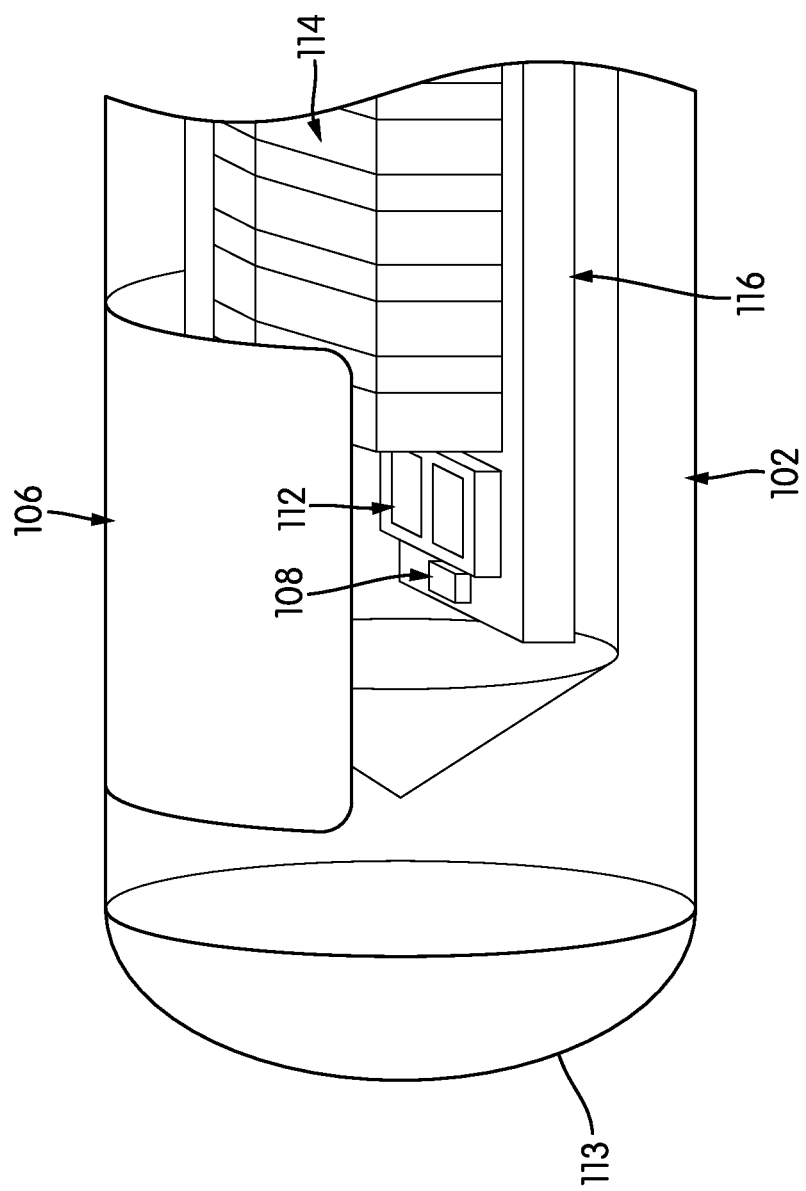
FIG. 2 is a partial side perspective view of an optical sensor of the type in which an optical isolation element may be employed.
Figure 3:
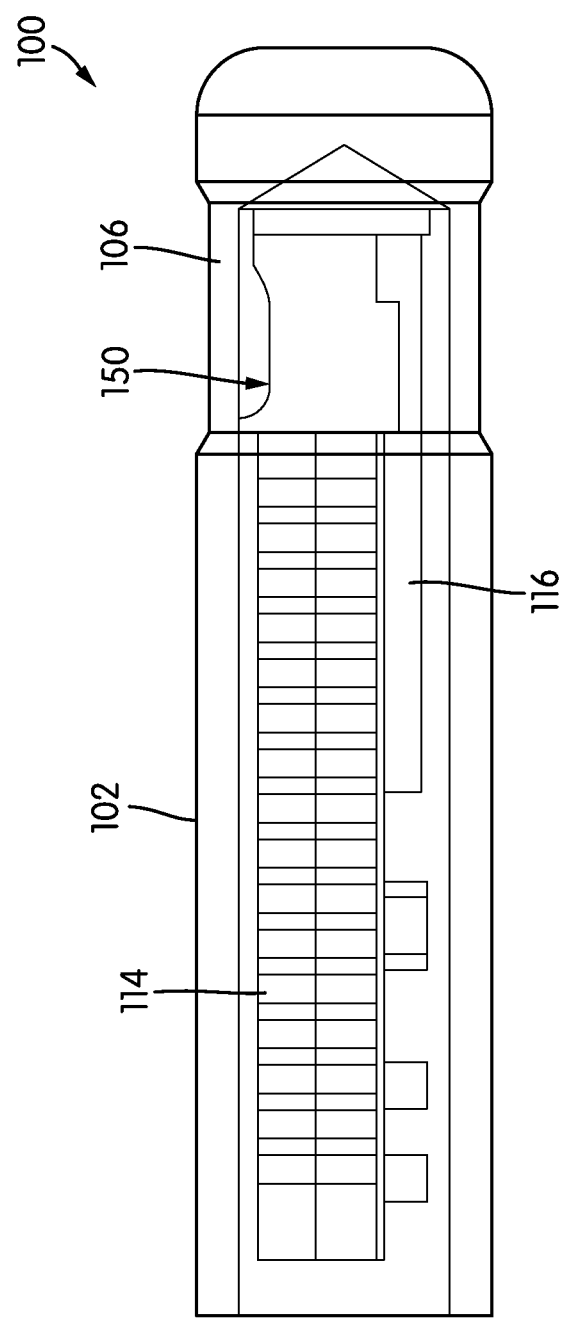
FIG. 3 is a side view of a sensor with an optical isolation element mounted thereon.
Figure 4:
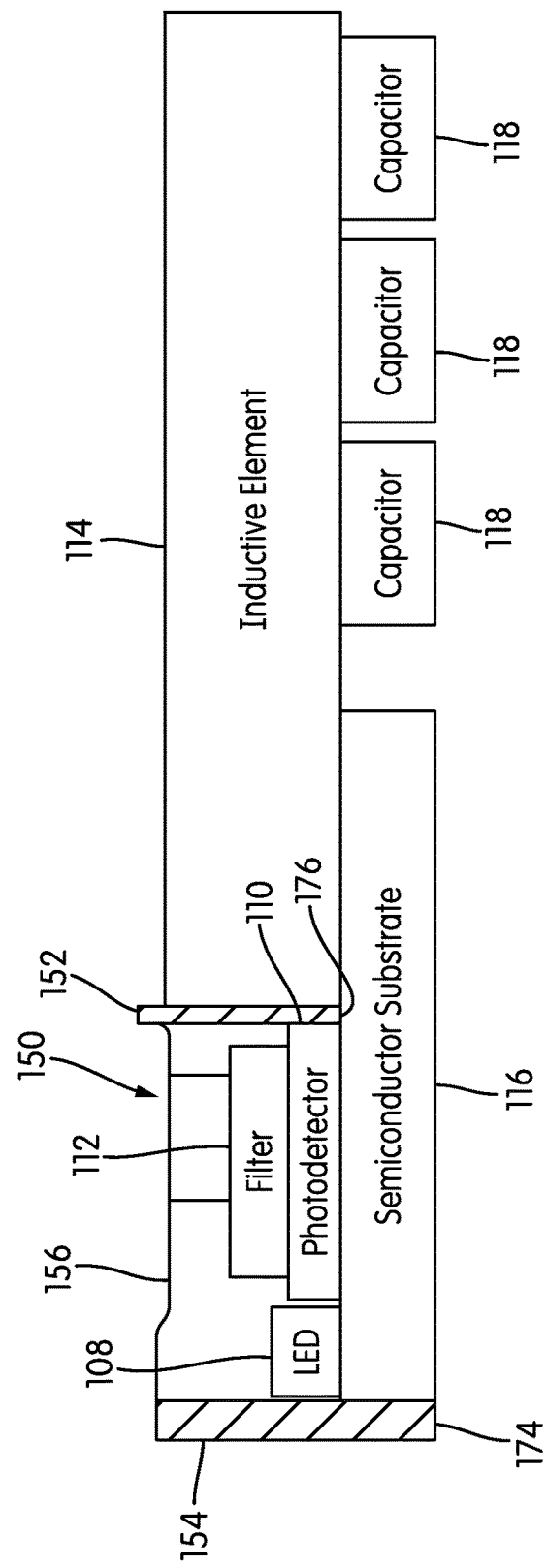
FIG. 4 is a side view of the internal components of the sensor and the optical isolation element shown in cross section.
Figure 5:
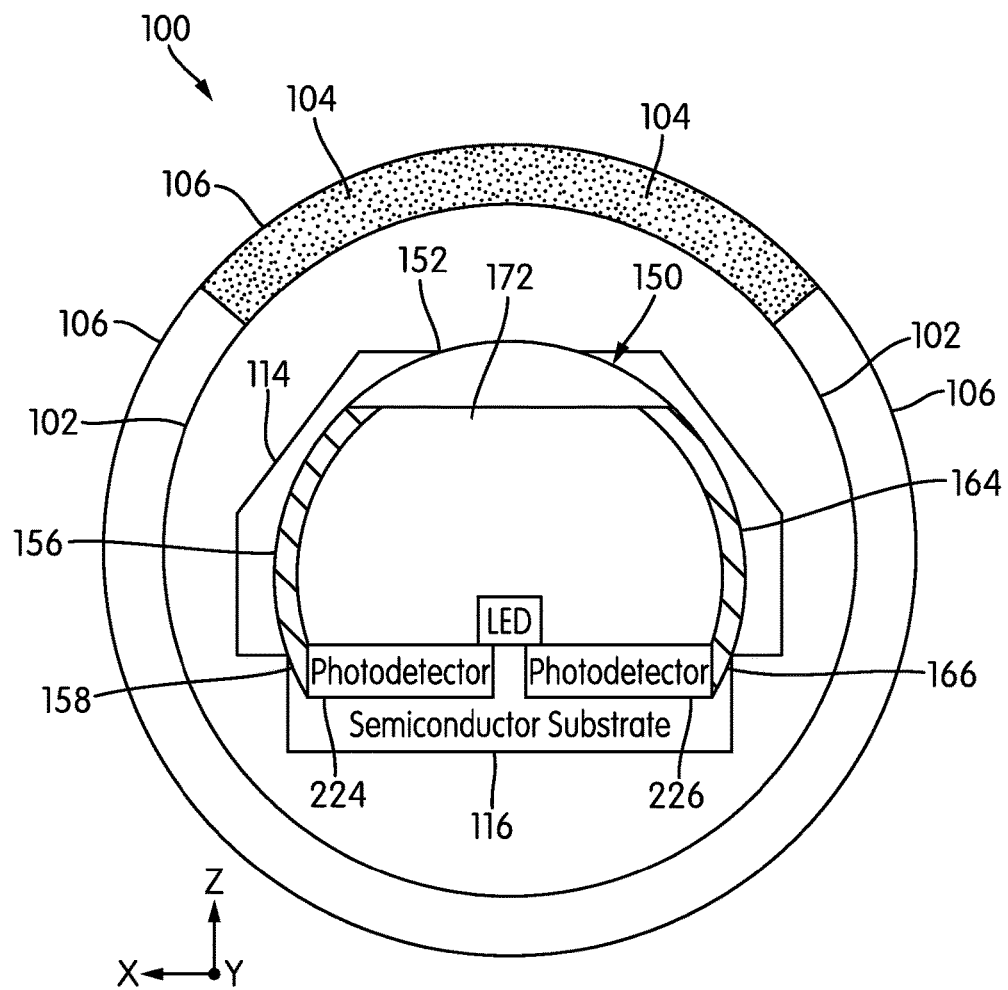
FIG. 5 is a transverse cross-sectional view of the sensor and optical isolation element.
Figure 6A:
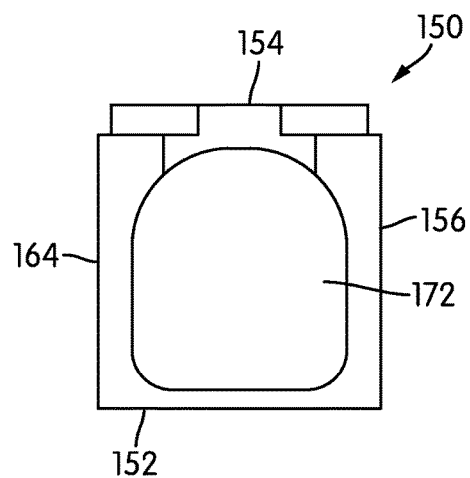
FIGS. 6A, 6B, 6C, and 6D are top, end, bottom, and right side views, respectively, of the optical isolation element.
Figure 6B:
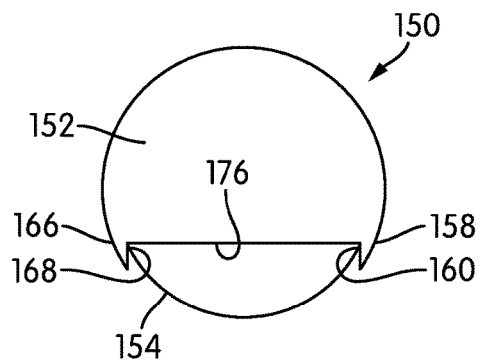
Figure 6C:
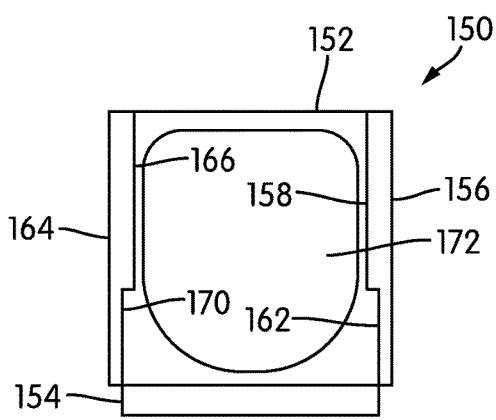
Figure 6D:
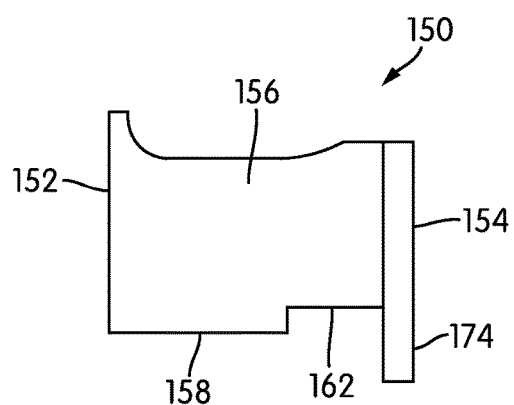

FIGS. 1 and 2 are an exploded perspective view and partial side perspective view, respectively, showing an optical sensor 100 of the type in which an optical isolation element embodying aspects disclosed herein may be employed. FIG. 3 is a side view of a sensor 100 with an exemplary optical isolation element 150 mounted thereon. FIG. 4 is a side view of the internal components of the sensor and the optical isolation element 150 is shown in cross-section. FIG. 5 is a transverse cross-sectional view of the sensor 100 and optical isolation element 150.

The sensor 100 may include a sensor housing 102 (i.e., body, shell, sleeve, or capsule). See, for example, FIGS. 1-3. The sensor housing 102 may include an end cap 113. In exemplary embodiments, sensor housing 102 may be formed from a suitable, optically transmissive polymer material, such as, for example, acrylic polymers (e.g., polymethylmethacrylate (PMMA)).

The sensor 100 may include an indicator matrix layer 106 (e.g., graft or gel) coated on or embedded in at least a portion of the exterior surface of the sensor housing 102. The sensor 100 may include indicator molecules 104, such as fluorescent indicator molecules or absorption indicator molecules distributed throughout all or a portion of the indicator matrix layer 106. The indicator matrix layer 106 may cover the entire surface of sensor housing 102 or only one or more portions of the surface of housing 102. Furthermore, as an alternative to coating the indicator matrix layer 106 on the outer surface of sensor housing 102, the indicator matrix layer 106 may be disposed on the outer surface of the sensor housing 102 in other ways, such as by deposition or adhesion.

In some sensors including an indicator matrix layer 106, the indicator matrix layer 106 may comprise a biocompatible polymer matrix that is prepared according to methods known in the art and coated on the surface of the sensor housing 102. In certain sensors, the biocompatible matrix materials are permeable to an analyte or substance of interest. Exemplary biocompatible matrix materials that may be used include some methacrylates (e.g., HEMA) and hydrogels that, advantageously, can be made selectively permeable—particularly to the analyte—so as to perform a molecular weight cut-off function. In a sensor that does not include an indicator matrix layer 106, instead of being distributed throughout an indicator matrix layer 106, the indicator molecules 104 could simply be coated on the surface of the sensor housing 102.

The sensor 100 includes one or more light sources 108 (a single light source is shown in the figures), which may, for example, comprise a light emitting diode (LED) or other light source that emits radiation, including radiation over a range of wavelengths that interact with the indicator molecules 104. For example, in the case of a fluorescence-based sensor, light source 108 emits radiation at a wavelength which causes the indicator molecules 104 to fluoresce when the indicator molecules are in the presence of an analyte or substance of interest. However, other LEDs or light sources may be used depending on the specific indicator molecules applied to sensor 100 and the specific analytes or substances of interested to be detected.

Sensor 100 also includes one or more photodetectors 110 (e.g., photodiodes, phototransistors, photoresistors or other photosensitive elements) which, in the case of a fluorescence-based sensor, is sensitive to fluorescent light emitted by the indicator molecules 104 such that a signal is generated by the photodetector 110 in response thereto that is indicative of the presence or level of fluorescence of the indicator molecules. The illustrated sensor 100 includes a first photodetector 224 and a second photodetector 226.

The sensor 100 may include one or more optical filters 112, such as high pass or band pass filters. The one or more optical filters 112 may cover a photosensitive side of the one or more photodetectors 110. The one or more optical filters 112 may prevent or substantially reduce the amount of radiation generated by the light source 108 from impinging on a photosensitive side of the one or more photodetectors 110. At the same time, the one or more optical filters 112 may allow light (e.g., fluorescent light) of a specified wavelength, or within a specified range of wavelengths, emitted by indicator molecules 104 to pass through and strike the photosensitive side of the one or more photodetectors 110. This reduces "noise" attributable to incident radiation from the light source 108 in the light measurement signals output by the one or more photodetectors 110. An optical isolation element such as described herein may be used in conjunction with or as an alternative to such optical filters 112.

Sensor 100 may be wholly self-contained. In other words, the sensor may be constructed in such a way that no electrical leads extend into or out of the sensor housing 102 to supply power to the sensor (e.g., for driving the light source 108) or to transmit signals from the sensor 100. Instead, in one embodiment, the sensor 100 may be powered by an internal, self-contained power source, such as, for example, microbatteries, micro generators and/or other power sources. However, in one preferred embodiment, sensor 100 may be powered by an external power source (not shown). For example, the external power source may generate a magnetic field to induce a current in an inductive element 114 (e.g., a coil or other inductive element). Additionally, the sensor 100 may use the inductive element 114 to communicate information to an external data reader (not shown). In some embodiments, the external power source and data reader may be the same device.

Sensor 100 may include a semiconductor substrate 116. In an illustrated embodiment, the circuitry is fabricated in the semiconductor substrate 116. The circuitry may include analog and/or digital circuitry. In a non-limiting embodiment, the circuitry may be formed in the semiconductor substrate 116 using a complementary metal oxide semiconductor (CMOS) process. However, other formation processes (e.g., n-type metal-oxide-semiconductor (NMOS) or n-type metal-oxide-semiconductor (PMOS)) may alternatively be used.

The one or more photodetectors 110 may be mounted on the semiconductor substrate 116, or, alternatively, the one or more photodetectors 110 may be fabricated in the semiconductor substrate 116. For example, in a non-limiting embodiment, the one or more photodetectors 110 may be monolithically formed in the semiconductor substrate 116. For instance, in one embodiment, the one or more photodetectors 110 may be monolithically formed in the semiconductor substrate 116 using a complementary metal oxide semiconductor (CMOS) process (e.g., using diffusions from the CMOS process). However, other formation processes (e.g., NMOS or PMOS) alternatively may be used.

The light source 108 may be mounted on the semiconductor substrate 116. For example, in a non-limiting embodiment, the light source 108 may be flip-chip mounted on the semiconductor substrate 116. Alternatively, the light source 108 may be fabricated in the semiconductor substrate 116.

Sensor 100 may also include one or more capacitors 118. The one or more capacitors 118 may be, for example, one or more antenna tuning capacitors and/or one or more regulation capacitors. Further, the one or more capacitors 118 may be in addition to one or more capacitors fabricated in the semiconductor substrate 116.

An application for which the sensor 100 was developed—although by no means the only application for which it is suitable—is measuring various biological analytes in the living body of an animal (including a human). For example, sensor 100 may be used to measure glucose, oxygen, toxins, pharmaceuticals or other drugs, hormones, and other metabolic analytes in, for example, the human body. The specific composition of the indicator matrix layer 106 and the indicator molecules 104 may vary depending on the particular analyte the sensor is to be used to detect and/or where the sensor is to be used to detect the analyte (e.g., in the blood or subcutaneous tissues). Preferably, however, indicator matrix layer 106, if present, should facilitate exposure of the indicator molecules to the analyte. Also, it is preferred that the optical characteristics of the indicator molecules (e.g., the level of fluorescence of fluorescent indicator molecules) be a function of the concentration of the specific analyte to which the indicator molecules are exposed.

To facilitate use in-situ in the human body, the sensor housing 102, in one embodiment, is preferably formed in a smooth, oblong or rounded shape. Other shapes and configurations could be used as well. Advantageously, in certain embodiments, the sensor 100 is on the order of approximately 500 microns to approximately 0.85 inches in length L and on the order of approximately 300 microns to approximately 0.3 inches in diameter D. In certain embodiments, the sensor 100 may have generally smooth, rounded surfaces. This configuration facilitates the sensor 100 to be implanted into the human body, i.e., dermally or into underlying tissues (including into organs or blood vessels) without the sensor interfering with essential bodily functions or causing excessive pain or discomfort. However, given its small size, the sensor 100 may have different shapes and configurations and still be implantable within a human without the sensor interfering with essential bodily functions or causing excessive pain or discomfort.

In exemplary configurations, a preferred length of the housing is approximately 0.5 inches to 0.85 inches and a preferred diameter is approx. 0.1 inches to 0.11 inches. However, in other embodiments, the housing may be even smaller.

FIGS. 3 and 4 are side views of the sensor 100 with an optical isolation element 150 mounted thereon. The optical isolation element 150 is mounted onto an end portion of the substrate 116 projecting from the inductor 114 and partially surrounds the light source 108, photodetectors 110, and optical filters (if present in the sensor) 112.

Figure 7:
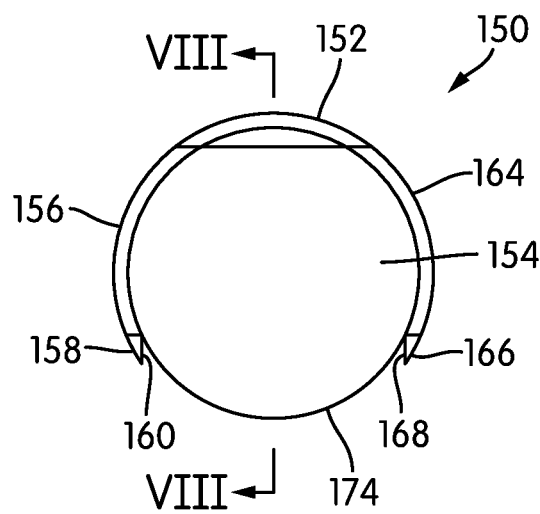
FIG. 7 is an end view of the optical isolation element.
Figure 8:
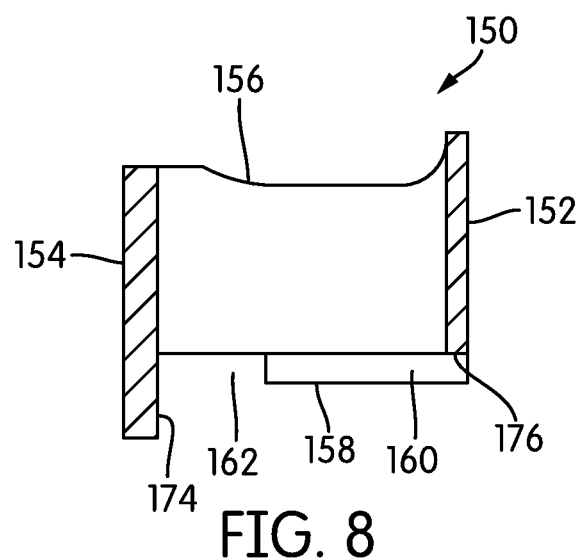
FIG. 8 is a cross-sectional view of the optical isolation element along the line VIII-VIII in FIG. 7.

Details of an exemplary optical isolation element 150 are shown in FIGS. 6, 7 and 8. The configuration of the optical isolation element is largely dependent upon the configuration and arrangement of the various components of the sensor, such as the inductor 114, the substrate 116, the light source 108, the photodetectors 110, and the filters 112, as well as the internal shape of the housing 102. The optical isolation element 150 shown in the figures is specifically configured so as to be compatible with the arrangement of the sensor 100. The configuration of the optical isolation element and the sensor are exemplary and are not intended to be limiting.

Referring to FIGS. 6, 7 and 8, the optical isolation element 150 includes a first end wall 152, an opposed second end wall 154, a first sidewall 156 extending between the first end wall 152 and the second end wall 154 and an opposed second sidewall 164 also extending between the first end wall 152 and the second end wall 154. An opening 172 is formed in a top portion of the optical isolation element 150. In one exemplary embodiment, the second end wall 154 has a generally circular shape, and the first end wall 152 has a partial circular shape with a flat bottom edge 176. The first sidewall 152 has a first sidewall extension 158 extending from a lower edge of the sidewall 152 and a cutout 162 adjacent to the extension 158. Similarly, the second sidewall 164 has a second sidewall extension 166 extending from a lower edge of the second side wall 164 and a cutout 174 adjacent to the extension 166. The first and second sidewalls 156, 164 have a curved, generally circular shape. As shown in FIGS. 6(b) and 7, the first sidewall extension 158 has a flattened surface 160, and the second sidewall extension 166 has a flattened surface 168.

FIGS. 4 and 5 show further details of an embodiment of the installation of the optical isolation element 150 on the sensor 100. In the illustrated embodiment, optical isolation element 150 is mounted on a portion of the semiconductor substrate 116 extending from the inductive element 114. The first end wall 152 is disposed against an end of the inductive element 114 with the flat edge 176 resting on the top surface of the semiconductor substrate 116. The second end wall 154 is disposed at an end of the semiconductor substrate 116 and includes a lower portion 174 extending below a top surface of the semiconductor substrate 116. End walls 152, 154 are generally parallel to each other and perpendicular to a longitudinal axis of the cylindrical sensor housing 102.

As shown in FIG. 5, the first sidewall 156 and the second sidewall 164 are disposed on opposite sides of the optical elements (photodetectors 224, 226 and light source (LED) 108) of the sensor 100 and partially enclose the photodetectors 226 and 224 and the light source 108. The sidewalls 156, 164 are generally circular in shape so as to conform to the circular cross-sectional shape of the housing 102. As shown in FIG. 5, the first sidewall extension 158 extends alongside the first photodetector 224 with the flattened portion 160 of the extension 158 providing a light-tight fitting between the sidewall 156 and the photodetector 224. Similarly, the sidewall extension 166 of the second sidewall 164 is disposed against the second photodetector 226, and the flattened surface 168 of the second extension 166 provides a light-tight fitting between the sidewall 164 and the photodetector 226.

As shown in FIG. 3, in accordance with one non-limiting embodiment, the cutouts 162 and 170 of the first and second sidewalls 156, 164, respectively, rest upon the top surface of the substrate 116.

The optical isolation element can be machined or molded, and it can be made from any suitable material that is sufficiently opaque, is moldable or machinable, and is non-reactive with other components or materials within the sensor 100. Suitable materials include plastic, metal, acrylic, glass, porcelain, epoxies, nylon or Delrin. Undesired light paths between the optical isolation element 150 and the electronic components of the sensor 100 can be blocked or filled with opaque materials, such as overfills, underfills, epoxies, or paints. As can be appreciated from FIGS. 5 and 6, any light emitted by the light source 108 can only escape the optical isolation element 152 through the top opening 172 of the optical isolation element. Thus, light from the light source 108 impinges substantially only on the indicator matrix 106 and does not disperse into other portions of the sensor 100. Similarly, substantially the only light that will impinge upon the photodetectors 224, 226 can reach the photodetectors only through the opening 172 of the optical isolation element 150. Extraneous light from other sources, such as ambient light, is substantially prevented from reaching the photodetectors 224 and 226 by the optical isolation element 150.

While an optical isolation element has been described and shown in considerable detail with reference to certain illustrative embodiments, including various combinations and sub-combinations of features, those skilled in the art will readily appreciate other embodiments and variations and modifications thereof as encompassed within the scope of the present disclosure. Moreover, the descriptions of such embodiments, combinations, and sub-combinations is not intended to convey that an optical isolation element requires features or combinations of features other than those expressly recited in the claims. Accordingly, the present disclosure is deemed to include all modifications and variations encompassed within the spirit and scope of the following appended claims.

The invention claimed is:

1. A sensor for detecting the presence and/or concentration of a substance of interest comprising:
at least one excitation light source;
indicator material positioned and oriented with respect to said excitation light source to receive excitation light emitted from said excitation light source and configured to emit an optical signal when excited by the excitation light source and when contacted by the substance of interest;
one or more optical detector elements positioned and oriented with respect to said indicator material to receive at least a portion of the optical signal emitted by the indicator material; and
an optical isolation element partially surrounding said at least one excitation light source and said one or more optical detector elements and formed of an optical isolation material configured to substantially prevent the passage of light through the optical isolation material, said optical isolation element being positioned and oriented with respect to said at least one excitation light source, said one or more optical detector elements, and said indicator material and including an opening formed in the optical isolation material so as to permit at least a portion of the light emitted by the excitation light source to exit the optical isolation element and impinge upon the indicator material and to permit at least a portion of the light emitted by the indicator material to enter the optical isolation element and impinge upon said optical detector element.

2. The sensor of claim 1, further comprising a housing enclosing said at least one light source, said one or more optical detector elements, and said optical isolation element, wherein said indicator material is disposed on or embedded in at least a portion of said housing.

3. The sensor of claim 2, wherein said optical isolation element is at least partially shaped to conform to an inner surface of said housing.

4. The sensor of claim 3, wherein said housing has a cylindrical shape, and said optical isolation element comprises first and second end walls that are generally parallel to each other and oriented so as to be perpendicular to a longitudinal axis of said housing and first and second side walls, each extending between said first and second end walls and each being curved so as to conform to a curvature of said housing.

5. The sensor of claim 1, wherein said optical isolation material is an opaque material.

6. The sensor of claim 5, wherein said optical isolation material is a material selected from the group consisting of: plastic, metal, acrylic, glass, porcelains, epoxies, Delrin, or nylon.

7. The sensor of claim 1, wherein said optical isolation element comprises first and second opposed end walls and first and second opposed side walls.

8. The sensor of claim 1, further comprising a planar substrate on which said at least one light source and said one or more optical detector elements are mounted, wherein said optical isolation element is cooperatively attached to said substrate so as to substantially prevent light from passing between said optical isolation element and said substrate.

9. The sensor of claim 1, wherein gaps between said optical isolation element and other components of the sensor are filled with opaque materials.

* * * * *